United States Patent [19]

Yarossi et al.

[11] Patent Number: 4,518,553
[45] Date of Patent: May 21, 1985

[54] PROCESS FOR PRODUCING A WAX-LIKE STICK PRODUCT

[75] Inventors: Mary E. Yarossi, Hoboken; Carey S. Trevisan, W. Orange, both of N.J.

[73] Assignee: American Cyanamid Co., Stamford, Conn.

[21] Appl. No.: 534,534

[22] Filed: Sep. 22, 1983

[51] Int. Cl.³ .................... B29C 5/00; B29C 27/30; B29C 25/00
[52] U.S. Cl. .................... 264/234; 264/267; 264/271.1; 264/279
[58] Field of Search .......... 264/267, 268, 250, 255, 264/25, 80, 263, 271.1, 279

[56] References Cited

U.S. PATENT DOCUMENTS 4,369,158  1/1983  Woodruff et al. .............. 264/268

FOREIGN PATENT DOCUMENTS 1408438  10/1975  United Kingdom .............. 264/267

Primary Examiner—Willard E. Hoag
Attorney, Agent, or Firm—Charles J. Fickey

[57] ABSTRACT

A process for producing a wax-like stick product by pouring molten ingredients into the open bottom of a container for the stick, cooling to partial solidification, heating to melt the upper surface, inserting a twist-up assembly in the open bottom which also closes the bottom, and cooling to solidify the stick product. The latter cooling is done in decreasing temperature stages.

9 Claims, 3 Drawing Figures

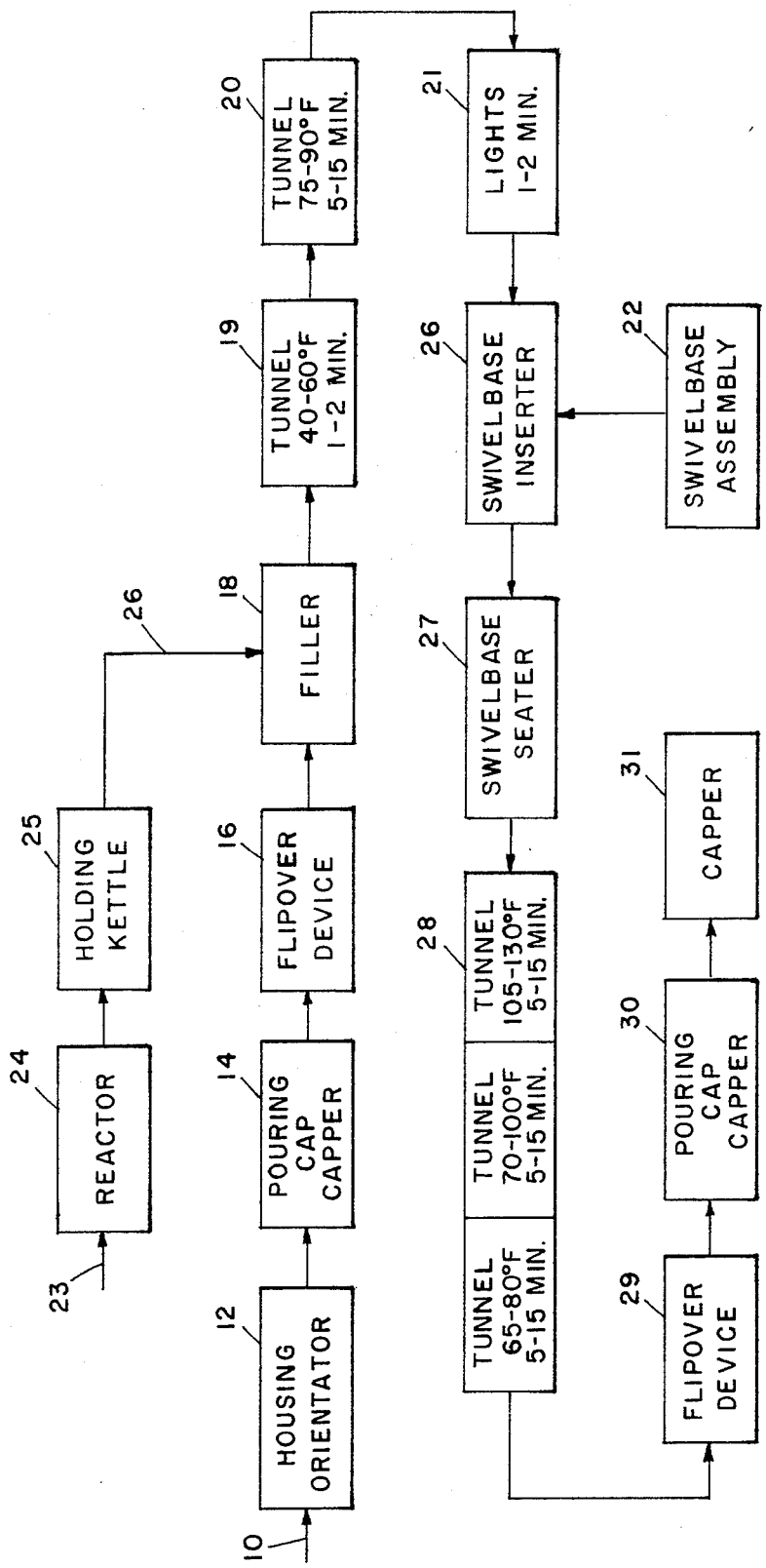

PROCESS FOR PRODUCING A WAX-LIKE STICK PRODUCT

This invention relates to a method for the manufacture of a solid, low melting, wax-like stick, e.g. a cosmetic or pharmaceutical stick in a twist-up type package. More particularly, it relates to an improved method for increasing the bonding strength between a plastic twist-up and the solid or semi-solid stick composition.

Most cosmetic sticks, including deodorant and antiperspirant compositions, comprise a solid, waxy, low melting formulation containing an active ingredient, where applicable, encased in a suitable container provided with a means for pushing the stick upwards through the container to expose more surface as the stick is consumed. Heretofore, as far as we are aware, these sticks, particularly deodorant and antiperspirant sticks, have been fabricated by pouring the molten composition into the top of a suitable container equipped with a suitable twist-up device inserted into the bottom thereof. In so doing, a pouring cup, open at the top, or pouring device, is first attached to the top of the container in a removable manner.

The method described results in a product having a number of disadvantages. A top surface is formed on the stick which is substantially perpendicular to the longitudinal axis of the stick, thereby forming a squared edge. When this edge is applied to a surface, it results in crumbling, with resultant loss of material until a rounded edge finally forms. In addition, during cooling and solidification of the stick material is poured in the container, the top surface contracts leaving air voids creating an unfavorable effect esthetically in the mind of the user.

It has also been proposed to form such an antiperspirant stick by a process in which the container is first fitted with a pouring cap, inverted and filled with the molten material through the open bottom of the container. Before the molten material is cooled, a twist-up device was inserted through the bottom of the container to contact the base of the solid cosmetic stick, the pouring cap was removed, and a regular package cap fitted to the container. Although this process formed a uniform shaped top to the cosmetic stick, it did not produce a firm bond between the base of the stick and the twist-up. The result was that the stick often separated from the twist-up and fell out of the container. In addition, large voids or shrink holes were formed in the base of the stick, depressions formed on the outer surface of the stick.

The present invention is an improvement over the prior process, whereby the bond strength between the push-up and the stick composition is improved; the shrink hole and air bubble formation are reduced; better control on the insertion of the housing component to be bonded with the stick is obtained; better control of the state of the stick prior to and during insertion is obtained; ripping of heads is reduced; there is manufacturing speed; and minimization of the effects of line breakdowns and variability of product are achieved.

The invention may be better understood by reference to the drawings in which:

FIG. 3 is a flow diagram of the process of the invention.

With reference to the flow sheet of FIG. 3, a reactor 22 is charged via line 20 with the ingredients to prepare the cosmetic stick formulation, which is then held until needed in a heated holding kettle 24.

Figure 1:
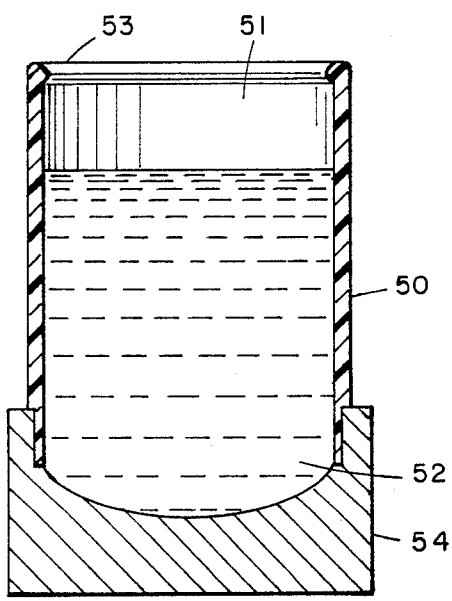
FIG. 1 is a cross-sectional view in elevation of a container and pouring head filled with molten fill material.
Figure 2:
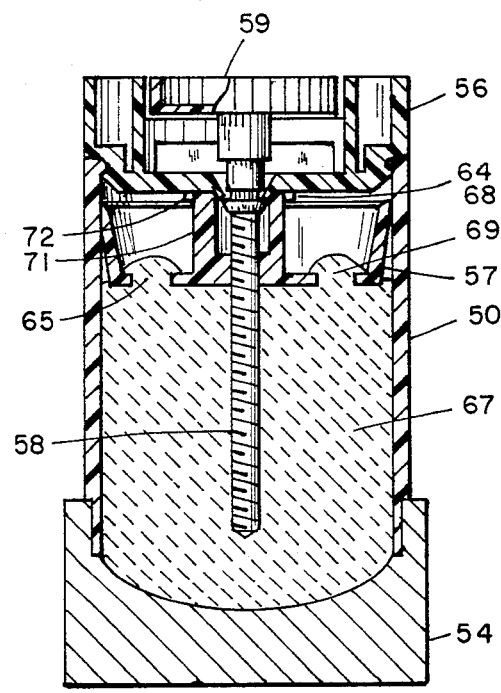
FIG. 2 is the container of FIG. 1 with a twist-up assembly inserted and the fill material solidified.

In a continuous manner a housing orientator 12 aligns the container bodies or housings 50 (See FIG. 1), which generally open at both top 51 and bottom 52 with a flange adjacent the bottom opening, in an upright position on a conveyor belt 10. Container housing then moves to a pouring cap affixing or capping device 14 which affixes onto the top of the housing a pouring cap 54, which closes the top end of the housing. The interior surface of pouring cap 54 is shaped to form a custom upper surface of the stick. Contaienr housings 50 are then inverted by a flipover device 16, after which a premeasured quantity of the molten formulation from holding kettle 24 at a temperature of about 53° C. is then added to contaier 50 through the bottom opening 51 by filling device 18 via line 26. Molten sticks in containers then pass in a single file through a cooling tunnel 19. Cool air is passed through tunnel 19 at a tempertures of from 40° F. to 60° F. for a period of about 1 to 2 minutes to form a skin of solid product on the tops of the sticks. This skin prevents liquid product from spilling over the sides of the housings 50 while traveling to conditioning tunnel 20. Sticks then pass through a first conditioning tunnel 20 for 5 to 15 minutes. A residence time of 10 minutes for tunnel temperature of 80° F. is preferred. The tunnel temperature may range from 70°-90° F. This conditioning step allows for partial solidifcation of the stick. A void is formed during this step. If adequate solidification does not occur in this step, the void will not form and further conditioning cannot eliminate the void. If too much solidification occurs during this step, melting, which is the next step may not be adequate to allow molten product to flow around the spindle assemby to form an anchor. The result would be a large void, a poos bond, or both.

After emerging from the first conditioning tunnel 20, sticks pass under a radient heat source 21. The top surface of the stick is melted and the void, formed in the previous step, is filled in. Melting of the crust is dependent on the type of heating elements, their distance from the top of the sticks, their intensity and the stick residence time under the elements. All of these parameters must be adjusted to result in a stick temperature of 49°-53° C. Sticks will generally be under the heat source for from 1 to 2 minutes.

If the top crust is not adequately melted, the void will not be filled. In addition, there will not be enough liquid to flow around the elevator to frm an anchor. Too much melting may result in the formation of another void upon further conditioning. Again, the result is either a large hole, a poor bond, or both.

Immediately after the molten material has been filled in case 50 (i.e. within about one minute), a twist-up assembly 55 preassembled at 22 is inserted into at bottom opening 51 by inserter 26 while the top of fill material is still melted. Twist-up assembly 55 consists of base plateform 56, elevator 57 and spindle 58 with knob 59. Spindle 58 fits through opening 60 of base 56 and is held in place by yieldable tabs 61 which fit into annular groove 62 on the shaft of spindle 58. Elevator 57 has a threaded central opening 63 which fits onto threaded spindle 58. Both base 56 and elevator 57 have ventilation openings 64 and 65 respectively for passage of air.

This is necessary so that the trapped air may escape from case 50 when the twist-up assembly 55 is inserted, to prevent formation of voids in the fill material after solidification. In addition, as the fill material begins to solidify, an internal vacuum develops and the vent holes provide for the reentry of air to relieve this to prevent dimple formation on the solidified stick surface next to the inner surface of case 50.

Spindle assembly 55 is inserted slowly at a controlled rate at low pressure by means of a compression belt by seater 27 to prevent splashing of molten material, and sealing of vent holes 65 in elevator 57 and prevent proper circulation of air. This also prevents deformation of the sticks. Base 56 has an annular groove 66 into which flange 53 of case 50 locks, to hold the twist-up assembly 55 in case 50. Container 50 then traverses a second tunnel 28 solidification zone where it solidifies to form the stick product. The second tunnel consists of three stages. This step provides for a staged cooling of the stick. This staged cooling prevents a void from reforming. Preferred residence time in tunnel 28 is 25 minutes, with a residence time of about 8 minutes in each tunnel section. Sticks should be in tunnel 28 for at least 15 minutes but should not remain more than 60 minutes. Container 60 passes through a first section whose temperature may range from 105°–130° F., with a preferred temperature of 120° F. The temperature range of the next section is 70° to 100° F. with a preferred temperature of 95° F. The temperature in the last section of this tunnel ranges from 65° to 80° F., with a preferred temperature of 80° F.

Upon emerging from tunnel 28, the stick in container 50 will be completely solidified. If temperatures in any of these sections are too high the stick may not be solid. In addition, high temperatures in the first section may widen the distribution of the active antiperspirant compound within the stick. If temperatures in this section are too low, a void may be formed. A decrease in residence time may also result in sticks not being solid. If sticks are not adequately solidified at this point in the process they cannot be packed in cartons immediately, instead they will have to be inverted and held this way until they solidify. Also stick heads may be cracked or damaged when pouring caps 54 are removed. After emerging from tunnel 28, the sticks are solidified, container 50, inverted by a flipover device 36 and then travels to an uncapping device 38 which removes pouring cap 54 from the top of container 50. Finally, the container is capped by the capper device 40. The finished sticks are then packed in cartons.

The shape of the top surface of the stick will depend on the design of the mold inserted into the pouring cap. Such designs may include lettering etched into the mold surface to depict the product name or company logo, and the like. Moreover, the mold may provide a tapered edge to the top edge of the stick whereby crumbling of the stick is prevented during use.

The container package of the invention is particularly useful for the preparation of deodorant and antiperspirant sticks, but may be used effectively for other cosmetic or pharmaceutical formulations in stick form.

In order to show the advantages of the package and process a comparison was made of cosmetic sticks formed under differing conditions, wherein the product ingredients were identical. The formulation was as follows:

|  | Parts by Weight |
|---|---|
| Ethoxylated Stearyl Alcohol | 1.0 |
| Stearyl Alcohol (95%) | 20.0 |
| Aluminum Chlorhydrate | 25.0 |
| Cyclic Silicone Pentamer | 53.0 |
| Fragrance | 0.6 |
|  | 100.0 |

Table I shows a comparison of processes to prepare (1) a cylindrical, push-up packaged antiperspirant stick, as described in copending commonly assigned application (2) an oval twist-up antiperspirant package described in another copending, commonly assigned application and and oval twist-up antiperspirant package as prepared by the process of the present invention. The previous application on the oval twist-up package was based on inserting the twist-up assemblies immediately after liquid product was filled into housings The process allowed a void to form in the stick as it cooled. Also, when there was a delay between filling the housing and inserting the twist-up assembly, the top layer of product could solidify. This slight solidification could prevent product from anchoring around the elevator and result in sticks which were poorly bonded. With the closed package of the prior application, the cooling rate was slowed. If a formulation with a low rate of heat transfer was to be processed this way, a long production time would be needed to solidify the stick.

The present invention calls for the stick to be partially solidified before the insertion of a twist-up assembly. A void is formed during this solidification. The top crust will be melted and the void filled. Twist-up assemblies can then be inserted. Melting of the top crust assures that liquid product will flow around the elevator, when the twist-up assemblies are inserted. This results in sticks with improved bond over the previous process. To prevent a void from reforming, sticks pass through a conditioning step which is a staged cooling process. At the end of this conditioning step, the sticks are solid.

TABLE I

| (1) Cylindrical Push-Up | (2) Prior Oval Twist-Up | (3) Present Oval Twist-Up |
|---|---|---|
| Insert first port of the 2-piece push up | N/A | N/A |
| Affix Pouring Cap | Affix Pouring Cap | Affix Pouring Cap |
| Bottom fill molten product into housing through push-up. | Bottom fill molten product into housing. | Bottom fill molten product into housing. |
| Pouring temp. 53 ± 1° C. | Pour temp. 53 ± 1° C. | Pour temp. 53 ± 1° C. |
| First conditioning step - Partial solidification 2.5–10 min., 59–77° F. | N/A | First conditioning step - Partial solidification 5–15 min., 75–95° F. |
| Remelt upper surface | N/A | Remelt upper surface. Stick temperature 49–53° C. |
| N/A | Insert spindle assembly | Insert spindle assembly |
| Second conditioning step - Complete solidification | Conditioning - 90–108° F., 12 min. 64–82° F., 12 min. | Second conditioning step: 105–130° F., 5–15 min. |

TABLE I-continued

| (1) Cylindrical Push-Up | (2) Prior Oval Twist-Up | (3) Present Oval Twist-Up |
| --- | --- | --- |
| 3–15 min., 59–77° F. | | 85–110° F., 5–15 min. |
| | | 70–90° F., 5–15 min. |
| Insert bottom plug in push-up | N/A | N/A |
| Remove pouring cap | Remove pouring cap | Remove pouring cap |
| Affix cap | Affix cap | Affix cap |
| Invert sticks - 3 hours | Invert sticks - 3 hours | Carton |

The cooling rate of the stick is faster with the present process since the majority of the solidification takes place when the package is open. With the process of the prior application, sticks were liquid at the end of the conditioning tunnel.

By allowing sticks to solidify before twist-up assemblies are inserted, according to the present invention, different kinds of baselocks can be used since the sides of the sticks will not be deformed.

In the process for the cylindrical sticks of prior application Ser. No. 505,653 filed 6/20/83, the sticks are partially solidified, the top crust melted to fill in voids and then further solidified. The cylindrical pacakge includes a push-up device instead of a twist-up mechanism. Molten product is filled into housings, into which the first part of the push-up has been inserted. Because of this, product anchoring to the push-up is assured, providing adequate fill weights are maintained. The degree of melting is not as critical to bonding as it is with the oval package with the twist-up assembly. Cooling is more uniform in the cylindrical package because of its shape. The cooling rate is also different with the cylindrical package. A staged cooling is not necessary in the second conditioning step. The remainder of the push-up device is not inserted until the top crust is re-solidified.

Thus it has been found that the process for the present oval twist-up package has a number of advantages over the process for the oval twist-up package of prior application Serial Number. The advantages are:
 a. Reduction in size and occurrance of internal voids.
 b. Improved product-to-elevator bond strength.
 c. Reduction of head rejects.
 d. Improved active distribution.
 e. Reduced time for solidification.

These advantages are illustrated in comparative Table II.

TABLE II

| | Previous Process | Present Remelt Process |
| --- | --- | --- |
| Ripped heads | 1.75 | 0.4 |
| Bond Strength (gms) | 190 | 466 |
| % No Holes | <5.0% | 61.0% |
| % Holes > 1.3 cm$^3$ | 2.31 | 0.22 |
| % Holes > 0.8 cm$^3$ | 7.34 | 4.64 |
| % Bad Bond (on-line testing) | 3.49 | 1.20 |
| Time to Cartoning Upright | 3 hrs. | 45 min. |
| Overall Line Rejects | 11.7% | 5.4% |

Bottom filling in the package of the invention also compensates for uneven filling. Thus it is not necessary to have as precise measuring of the quantity since the cavity 68 below elevator will allow for excess molten stick material.

As seen at 69, elevator 57 is pushed into the remelted material so that the material exudes through air holes 65. After solidification, the material locks the stick 67 more firmly to elevator 57. An additional lip, not shown, may be provided around the periphery of the upper surface 70 of elevator 57 to provide additional bonding for stick 67.

In addition, a key 71 is provided on the lower side of elevator 57 which fits into a pair of stops 72 on either side of the upper surface of base 56. This prevents turning of spindle 58 when in a fully retracted position and stripping the threaded fit between solid stick 67 and the spindle. Nibs 73 have been provided on the sides of elevator 57 to maintain continuous contract with the inner surface of case 50. This prevents separation of the stick from the elevator during retraction after the stick has been turned up for use, due to translated torque.

The present process and package make it possible to produce a stick which is homogeneous, free of voids and dimples, has less ripped heads, and has excellent bonding to the elevator in a twist-up, non-symmetrical package. In addition, since container 50 and base 56 are separable, the fill product weight may be varied by changing the height of container 50. Any height of the container will still fit the same base 56.

We claim:

1. A process for the manufacture of a solid, wax-like stick product, which comprises the steps of attaching a pouring cap closure to the upper portion of a suitable container for said stick, said container being open at the bottom; inverting said container body and filling from the bottom thereof with a premeasured quantity of wax-like composition in a molten state; cooling said stick to partially solidify it and form a void in an upper surface of said composition; heating said stick to melt the upper surface and fill in said void; inserting into the bottom portion of said container body before said upper surface solidifies, a twist-up device, cooling said composition for sufficient time to form within said container a solid, wax-like stick and re-inverting the container.

2. The process of claim 1 wherein said container filled with molten material is passed through a conditioning tunnel at a temperature of 75° to 90° F. for a time of 5 to 15 minutes to effect said partial solidification.

3. The process of claim 1 wherein said heating is done at a temperature of 110° to 140° F. for a time of about 1 to 2 minutes.

4. The process of claim 1 including the step of removing said pouring cap.

5. The process of claim 1 wherein said stick product contains cosmetic or pharmaceutical ingredients.

6. The process according to claim 1 wherein said container is a non-symmetriacal body adapted on the upper portion to receive a cap and having a flange incorporated in the bottom as a seat for said twist-up device.

7. The process of claim 6 wherein said twist-up comprises a base, spindle and elevator, both said base and elevator having air vents.

8. The process of claim 1 wherein said stick is cooled quickly following filling of said container to form a thin skin on the upper surface of said molten composition.

9. The process of claim 8 wherein said cooling to form said skin on said molten material is done in a tunnel at a temperature of 40° to 60° F. for a time of about 1 to 2 minutes.

* * * * *